(12) United States Patent
Lee

(10) Patent No.: US 8,813,763 B2
(45) Date of Patent: Aug. 26, 2014

(54) INTERDENTAL CLEANER

(71) Applicant: Sang Sook Lee, Jeonju-si (KR)

(72) Inventor: Sang Sook Lee, Jeonju-si (KR)

(\*) Notice: Subject to any disclaimer, the term of this patent is extended or adjusted under 35 U.S.C. 154(b) by 0 days.

(21) Appl. No.: 13/848,509

(22) Filed: Mar. 21, 2013

(65) Prior Publication Data

US 2013/0213432 A1 Aug. 22, 2013

Related U.S. Application Data

(63) Continuation-in-part of application No. 13/699,704, filed on Nov. 23, 2012, now abandoned.

(30) Foreign Application Priority Data

May 26, 2010 (KR) .................. 10-2010-0049275

(51) Int. Cl.
*A61C 15/00* (2006.01)
*A61C 15/04* (2006.01)

(52) U.S. Cl.
CPC ................................ *A61C 15/043* (2013.01)
USPC ........................................................ 132/325

(58) Field of Classification Search
USPC .................................................. 132/321–329
See application file for complete search history.

(56) References Cited

U.S. PATENT DOCUMENTS

| 3,747,611 | A | * | 7/1973 | Bennington | 132/325 |
| 3,908,678 | A | * | 9/1975 | Conn et al. | 132/325 |
| 4,901,742 | A | * | 2/1990 | Olson | 132/325 |
| 2005/0092347 | A1 | * | 5/2005 | Fan | 132/325 |

\* cited by examiner

*Primary Examiner* — Rachel Steitz
(74) *Attorney, Agent, or Firm* — Novick, Kim & Lee, PLLC; Jae Youn Kim

(57) ABSTRACT

An interdental cleaner which can firmly hold a dental floss that has been pulled out of a floss dispenser to a desired length, so that the interdental cleaner can prevent the floss from being further pulled out and can prevent a slip of the floss when a user uses the floss.

8 Claims, 17 Drawing Sheets

INTERDENTAL CLEANER

CROSS-REFERENCES TO RELATED APPLICATIONS

This application is a continuation-in-part (CIP) application of U.S. patent application Ser. No. 13/699,704 filed on Nov. 23, 2013, entitled "INTERDENTAL CLEANER," which is hereby incorporated by reference in its entirety.

TECHNICAL FIELD

The present invention relates, in general, to an interdental cleaner which can firmly hold a dental floss that has been pulled out of a floss dispenser to a desired length, so that the interdental cleaner can prevent the floss from being further pulled out and can prevent a slip of the floss when a user uses the floss.

BACKGROUND ART

Generally, an interdental cleaner is a tool that removes foul matter from teeth using a dental floss and typically includes a floss dispenser and a dental floss that is placed in the floss dispenser in a wound state.

To remove foul matter from teeth using a conventional interdental cleaner, the dental floss is pulled out of the floss dispenser to a desired length and is inserted into the mouth in a state in which the dental floss is held by one hand and the floss dispenser is held by the other hand.

However, when the dental floss is strongly pulled out of the floss dispenser of the conventional interdental cleaner, the floss may slip off because the floss dispenser does not firmly hold the floss, so that the conventional interdental cleaner is inconvenient to users.

DISCLOSURE

Technical Problem

Accordingly, the present invention has been made keeping in mind the above problems occurring in the related art, and is intended to provide an interdental cleaner which can firmly hold a dental floss that has been pulled out of a floss dispenser to a desired length, so that the interdental cleaner can prevent the floss from being further pulled out and can prevent a slip of the floss when a user uses the floss.

Technical Solution

In an aspect, the present invention provides an interdental cleaner, including: a dispenser body including a lower body having therein an upward open lower chamber, with a fixing shaft being vertically formed on a bottom surface of the lower chamber, and an upper body placed on the lower body and having therein a downward open upper chamber, with a through hole being formed through a top wall of the upper body so as to communicate with the lower chamber; a bobbin provided in the dispenser body in such a way that the bobbin is fitted over the fixing shaft of the dispenser body, with a dental floss being wound around the bobbin; an elastic member provided in the dispenser body; and a pressure unit provided in the dispenser body in such a way that the pressure unit can move upward and downward in the dispenser body by elasticity of the elastic member so that the pressure unit can control a rotation of the bobbin and an upper end of the pressure unit can protrude outside the dispenser body through the through hole of the dispenser body.

Here, vertical movement guide grooves may be vertically formed at regular intervals around an outer circumferential surface of the fixing shaft of the dispenser body, and fixing grooves may be formed at regular intervals around an upper part of an inner circumferential surface of the bobbin, wherein the pressure unit may include: a pressure button that is vertically movably received in the bobbin so that an upper end of the pressure button protrudes outside the dispenser body through the through hole of the dispenser body, with vertical movement guide protrusions being formed at regular intervals around a lower part of an inner circumferential surface of the pressure button so as to be engaged with the vertical movement guide grooves of the fixing shaft; and fixing protrusions that are formed at regular intervals around a lower part of an outer circumferential surface of the pressure button so as to be engaged with the fixing grooves of the bobbin, and the elastic member may be provided in a lower part inside the dispenser body such that the elastic member is placed in the bobbin in a state in which the elastic member surrounds a lower end of the fixing shaft of the dispenser body so as to elastically support a lower end of the pressure button.

Further, vertical movement guide grooves may be vertically formed at regular intervals around an outer circumferential surface of the fixing shaft of the dispenser body, and fixing grooves may be formed at regular intervals around a lower part of an inner circumferential surface of the bobbin, wherein the pressure unit may include: a pressure button that is vertically movably received in the bobbin so that an upper end of the pressure button protrudes outside the dispenser body through the through hole of the dispenser body, with vertical movement guide protrusions being formed at regular intervals around a lower part of an inner circumferential surface of the pressure button so as to be engaged with the vertical movement guide grooves of the fixing shaft; and fixing protrusions that are formed at regular intervals around a lower part of an outer circumferential surface of the pressure button so as to be engaged with the fixing grooves of the bobbin, and the elastic member may be provided in an upper part inside the dispenser body such that the elastic member is placed in the bobbin in a state in which the elastic member surrounds the pressure button so as to elastically support upper ends of the fixing protrusions.

Further, fixing grooves may be formed at regular intervals on a lower surface of the top wall of the upper body that defines the upper chamber such that the fixing grooves are placed at locations around the through hole of the dispenser body, wherein the pressure unit may include: a pressure button that is vertically formed on a center of an upper surface of the bobbin and moves upward and downward in the dispenser body together with the bobbin so that an upper end of the pressure button protrudes outside the dispenser body through the through hole of the dispenser body; and fixing protrusions that are formed at regular intervals around an outer circumferential surface of an upper part of the pressure button in a state in which the fixing protrusions are integrated with the upper surface of the bobbin so that the fixing protrusions can be engaged with the fixing grooves of the dispenser body, and the elastic member may be placed in the dispenser body in a state in which the elastic member surrounds a lower part of the fixing shaft of the dispenser body so as to elastically support a lower surface of the bobbin.

In addition, fixing grooves may be formed on the bottom surface of the lower chamber of the lower body at regular intervals so that the fixing grooves are placed at locations around the fixing shaft of the dispenser body, wherein the pressure unit may include: a pressure button that is vertically formed on a center of an upper surface of the bobbin and moves upward and downward in the dispenser body together with the bobbin so that an upper end of the pressure button protrudes outside the dispenser body through the through hole of the dispenser body; and fixing protrusions that are formed at locations around a center of a lower surface of the bobbin at regular intervals in a state in which the fixing protrusions are integrated with the lower surface of the bobbin so that the fixing protrusions are engaged with the fixing grooves of the dispenser body, and the elastic member may be placed in the dispenser body in a state in which the elastic member surrounds the pressure button so as to elastically support the upper surface of the bobbin.

Further, a shaft may be vertically formed on a part of the bottom surface of the lower chamber of the dispenser body so that the dental floss of the bobbin can be wound around the shaft, and a tip may be provided in the dispenser body, with an outlet hole being formed in a first end of the tip so as to allow the dental floss wound around the shaft to be pulled out through the outlet hole.

Here, a second end of the tip may be combined with a first end of the dispenser body through a screw type engagement.

Further, a guide groove may be formed on an inner circumferential surface of a first end of the dispenser body by axially extending, a locking groove may be formed on the inner circumferential surface of the first end of the dispenser body by vertically extending from a second end of the guide groove so as to communicate with the guide groove, and a locking protrusion may protrude on an outer circumferential surface of a second end of the tip in a radially outward direction from the second end of the tip so that the locking protrusion can axially move along the guide groove and can be locked in the locking groove.

Further, an annular groove may be formed around an outer circumferential surface of the shaft so as to hold the dental floss.

In addition, a cutting member may be provided in an upper surface of a first end of the top wall of the upper body of the dispenser body so that the cutting member can cut the dental floss that has been pulled out of the dispenser body.

Advantageous Effects

As described above, the present invention is advantageous in that a pressure unit moves upward and downward in a dispenser body and controls the rotation of a bobbin so that the present invention can firmly hold a dental floss that has been pulled out of the dispenser body to a desired length, thereby preventing the dental floss from being further pulled out and preventing the dental floss from being undesirably pulled out when a user uses the floss, that is, the present invention preventing a slip of the dental floss.

Further, the present invention is advantageous in that it can more efficiently control the rotation of the bobbin using the pressure unit having both a pressure button and fixing protrusions.

In addition, the present invention is advantageous in that the dental floss is wound around a shaft that is vertically formed on the bottom surface of the lower chamber of the dispenser body so that the bobbin, which rotates reversibly during a floss pulling process in which the dental floss is pulled out of the dispenser body through an outlet hole of a tip, can be more efficiently prevented from moving upward and downward.

Further, the present invention is advantageous in that a second end of the tip is combined with a first end of the dispenser body through a screw type engagement so that the tip can be more simply and more firmly combined with the first end of the dispenser body.

Particularly, when both a guide groove and a locking groove are formed on the inner circumferential surface of the first end of the lower body of the dispenser body, and a locking protrusion is formed on the outer circumferential surface of the second end of the tip in such a way that, when the user axially moves the locking protrusion along the guide groove and rotates the locking protrusion, the locking protrusion can be locked in the locking groove, the tip can be more easily and more firmly assembled with the first end of the dispenser body through a one touch assembly process.

In addition, the dental floss is held in an annular groove, which is formed around the outer circumferential surface of the shaft, in a state in which the dental floss is wound around the annular groove, so that the dental floss can be more efficiently prevented from being removed from the shaft.

Further, the present invention is advantageous in that it can more easily cut the dental floss, which has been pulled out of the dispenser body, using a cutting member that is formed in the first end of the top wall of the upper body of the dispenser body.

MODE FOR INVENTION

Hereinbelow, preferred embodiments of the present invention will be described in detail with reference to the accompanying drawings. Of course, the scope and spirit of the present invention are not limited to the embodiments described hereinbelow, but the embodiments of the present invention may be changed to a variety of embodiments by those skilled in the art without departing from the scope and spirit of the invention.

Figure 1:
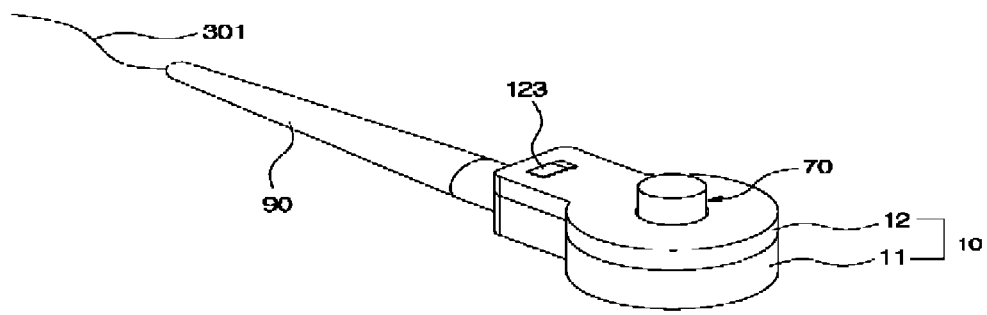
FIG. 1 is a perspective view schematically illustrating an interdental cleaner according to a first embodiment of the present invention.
Figure 2:
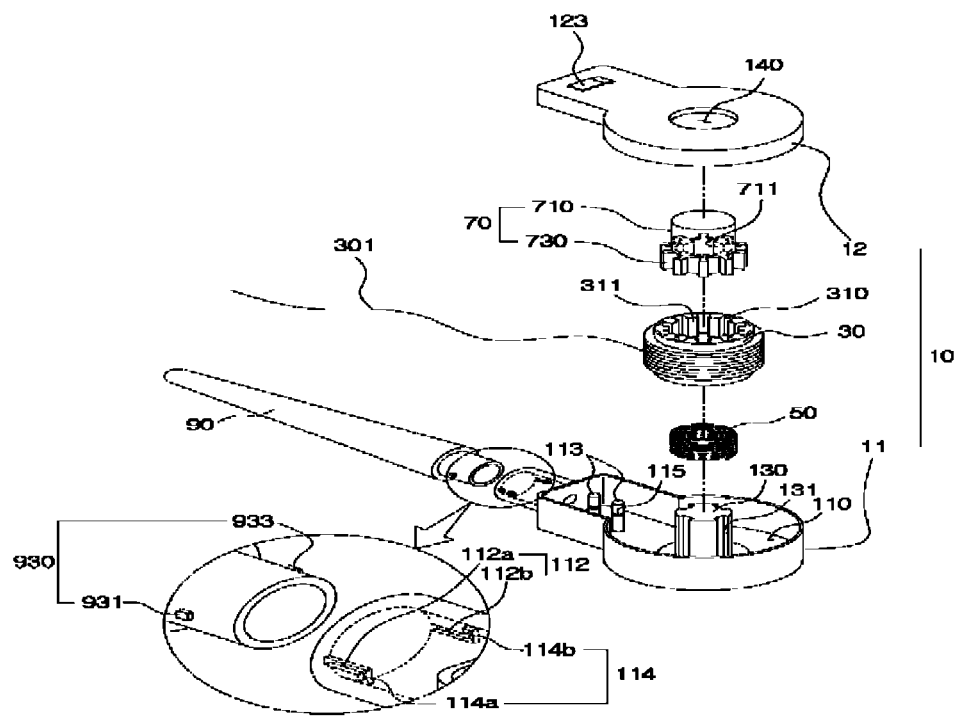
FIG. 2 is an exploded perspective view of FIG. 1.

FIG. 1 is a perspective view schematically illustrating an interdental cleaner according to a first embodiment of the present invention. FIG. 2 is an exploded perspective view of FIG. 1.

As shown in FIGS. 1 and 2, the interdental cleaner of the present invention includes a dispenser body 10, a bobbin 30, an elastic member 50 and a pressure unit 70.

First, the dispenser body 10 is fabricated with a lower body 11 and an upper body 12.

A lower chamber 110 (see FIG. 2) that is open upward is defined in the lower body 11.

A fixing shaft 130 is vertically formed on the bottom surface of the lower chamber 110.

The upper body 12 is removably assembled with the lower body 11 at a position above the lower body 11.

An upper chamber 120 (see FIG. 3) that is open downward is defined in the upper body 12.

In the upper body 12, a through hole 140 is formed through the center of the top wall of the upper body upper 12.

Second, the bobbin 30 is placed in the dispenser body 10 in a state in which the bobbin 30 is fitted over the fixing shaft 130 of the lower body 11 of the dispenser body 10 and can be reversibly rotated.

A dental floss 301 is wound around the outer circumferential surface of the bobbin 30.

Third, the elastic member 50 is placed in the dispenser body 10.

A spring and the like may be used as the elastic member 50, however, another elastic material may be used as the elastic member 50.

Further, the pressure unit 70 can move upward and downward in the dispenser body 10 by elasticity of the elastic member 50 so that the pressure unit 70 can control a reversible rotation of the bobbin 30.

The upper end of the pressure unit 70 protrudes outside the top wall of the upper body 12 of the dispenser body 10 through the through hole 140 of the upper body 12 of the dispenser body 10.

Further, as shown in FIG. 2, vertical movement guide grooves 131 may be vertically formed around the outer circumferential surface of the fixing shaft 130 of the lower body 11 of the dispenser body 10 at regular intervals. Here, the vertical movement guide grooves 131 are depressed to a predetermined depth in the fixing shaft 130 and extend in vertical directions.

Further, fixing grooves 310 may be formed around an upper part of the inner circumferential surface of the bobbin 30 at regular intervals.

The fixing grooves 310 may be defined between partition ridges 311 that are vertically formed around an upper part of the inner circumferential surface of the bobbin 30 at regular intervals.

The pressure unit 70 may include a pressure button 710 and fixing protrusions 730.

The pressure button 710 may be inserted into the center hole of the bobbin 30 so that the pressure button 710 can move upward and downward.

The upper end of the pressure button 710 may protrude outside the top wall of the upper body 120 of the dispenser body 10 through the through hole 140 of the upper body 12 of the dispenser body 10.

The lower part of the pressure button 710 may be open downward, with vertical movement guide protrusions 711 being vertically formed around the inner circumferential surface of the open lower part of the pressure button 710 at regular intervals so that the vertical movement guide protrusions 711 protrude inward in the pressure button 710 in radial directions.

The vertical movement guide protrusions 711 of the pressure button 710 may be engaged with the vertical movement guide grooves 131 of the fixing shaft 130 of the lower body 11.

Here, the fixing protrusions 730 protrude outward from the lower part of the pressure button 710 in radial directions so that the fixing protrusions 730 may be vertically formed around the outer circumferential surface of the lower part of the pressure button 710 at regular intervals.

The fixing protrusions 730 may be engaged with the fixing grooves 310 of the bobbin 30.

To elastically support the lower end of the pressure button 710, the elastic member 50 may be vertically placed in the lower part of the dispenser body 10 in a state in which the elastic member 50 is received in the bobbin 30 that is fitted over the lower part of the fixing shaft 130 of the lower body 11 of the dispenser body 10.

Figure 3:
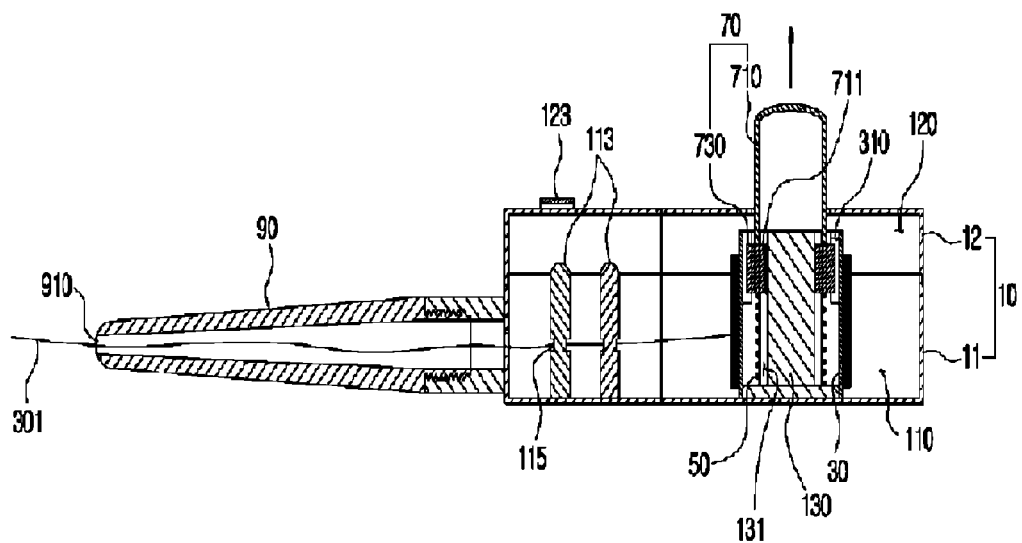
FIGS. 3 and 4 are sectional views schematically illustrating a process of pulling a dental floss out of a dispenser body of FIG. 1.
Figure 4:
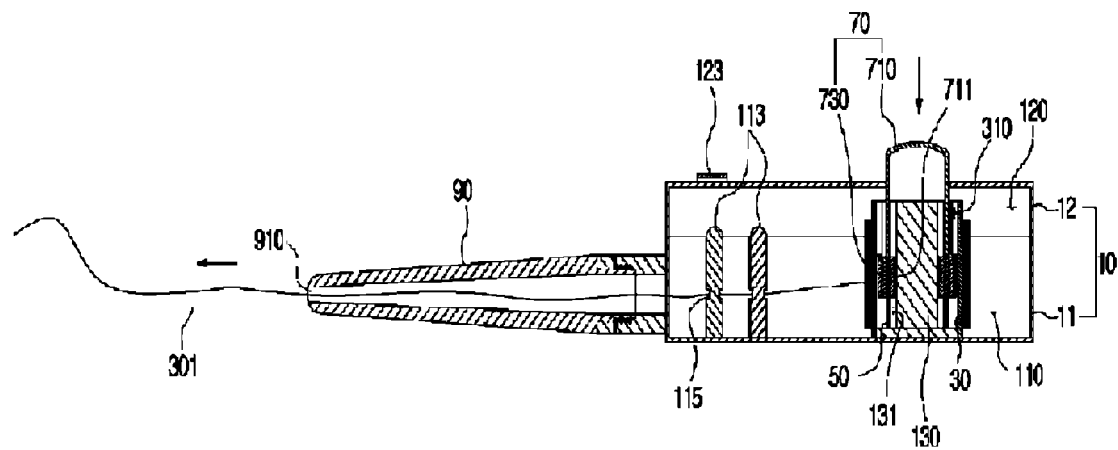

FIGS. 3 and 4 are sectional views schematically illustrating a process of pulling the dental floss 301 out of the dispenser body 10 of FIG. 1.

As shown in FIGS. 3 and 4, when a user presses the pressure button 710 of the pressure unit 70 downward, the pressure button 710 having both the fixing protrusions 730 and the vertical movement guide protrusions 711 moves downward in a direction toward the lower body 11 along the vertical movement guide grooves 131 of the fixing shaft 130 while compressing the elastic member 50.

When the pressure button 710 moves downward as described above, the fixing protrusions 730 are disengaged from the fixing grooves 310 of the bobbin 30 so that the bobbin 30 can rotate reversibly.

In the above state, when the user pulls the dental floss 301 that is exposed outside the dispenser body 10 out of the dispenser body 10, the bobbin 30 rotates reversibly and the dental floss 301 can be pulled out of the dispenser body 10 to a desired length.

When the user removes the pressing force from the pressure button 710 of the pressure unit 70, the elastic member 50 elastically expands so that the pressure button 710 having both the fixing protrusions 730 and the vertical movement guide protrusions 711 moves upward in a direction toward the upper body 12 along the vertical movement guide grooves 131 of the fixing shaft 130 by the expansion force of the elastic member 50.

When the pressure button 710 moves upward as described above, the fixing protrusions 730 are brought into engagement with the fixing grooves 310 of the bobbin 30 so that the bobbin 30 cannot rotate reversibly.

Here, because the bobbin 30 cannot rotate reversibly as described above, the dental floss 301 is prevented from being pulled out of the dispenser body 10.

Figure 5:
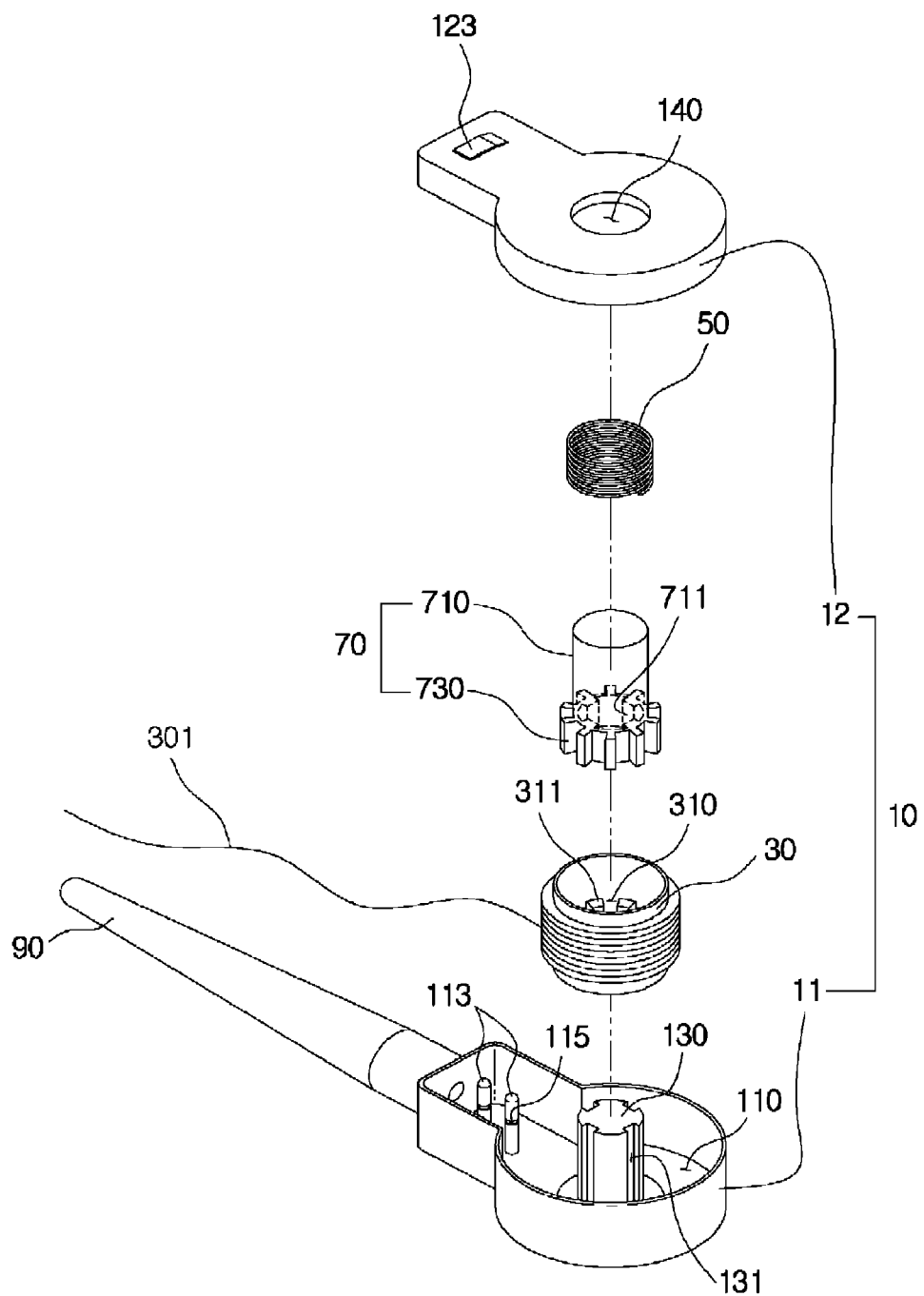
FIG. 5 is an exploded perspective view schematically illustrating an interdental cleaner according to a second embodiment of the present invention.
Figure 6:
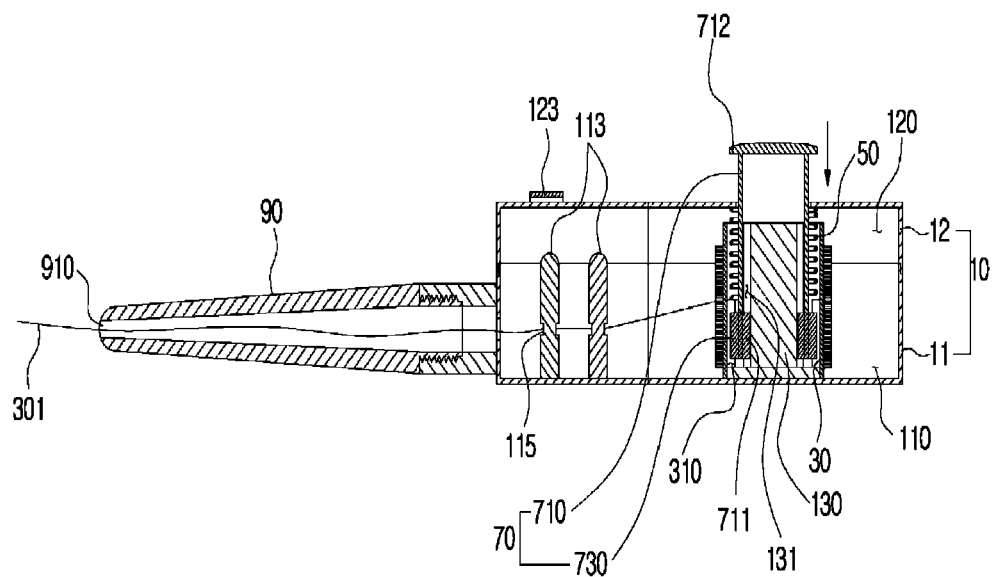
FIGS. 6 and 7 are sectional views schematically illustrating a process of pulling a dental floss out of a dispenser body of FIG. 5.
Figure 7:
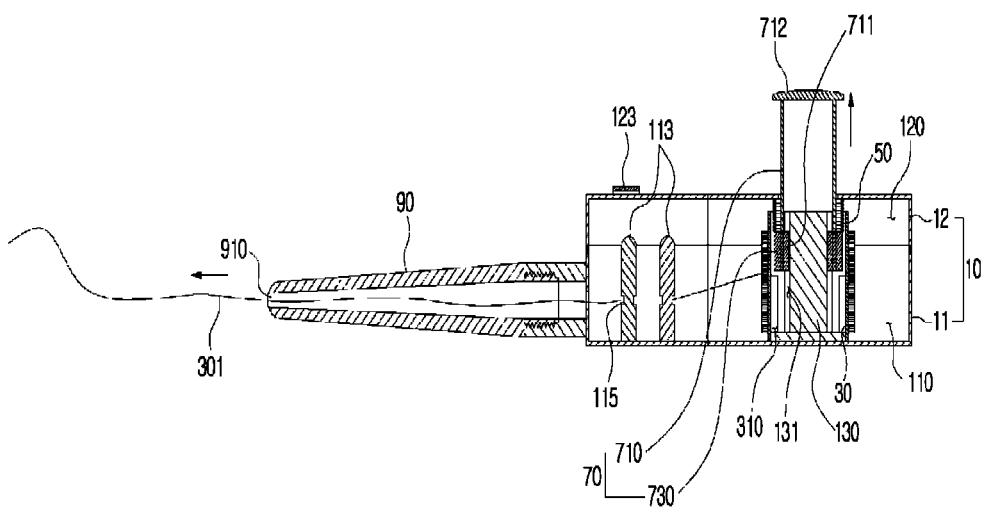

FIG. 5 is an exploded perspective view schematically illustrating an interdental cleaner according to a second embodiment of the present invention. FIGS. 6 and 7 are sectional views schematically illustrating a process of pulling a dental floss out of a dispenser body of FIG. 5.

As shown in FIG. 5, vertical movement guide grooves 131 may be vertically formed around the outer circumferential surface of the fixing shaft 130 of the lower body 11 of the dispenser body 10 at regular intervals. Here, the vertical movement guide grooves 131 are depressed to a predetermined depth in the fixing shaft 130 and extend in vertical directions.

As shown in FIGS. 6 and 7, fixing grooves 310 may be formed around a lower part of the inner circumferential surface of the bobbin 30 at regular intervals.

The fixing grooves 310 may be defined between partition ridges 311 that are vertically formed around a lower part of the inner circumferential surface of the bobbin 30 at regular intervals.

The pressure unit 70 may include a pressure button 710 and fixing protrusions 730 in the same manner as described above.

As shown in FIGS. 5 through 7, to elastically support the upper ends of the fixing protrusions 730, the elastic member 50 may be placed in the upper part of the dispenser body 10 in a state in which the elastic member 50 is received in the bobbin 30 while being fitted over the outer circumferential surface of the upper part of the pressure button 710.

As shown in FIGS. 6 and 7, when a user pulls the pressure button 710 of the pressure unit 70 upward, the pressure button 710 having both the fixing protrusions 730 and the vertical movement guide protrusions 711 moves upward in a direction to the outside of the top wall of the upper body 12 along the vertical movement guide grooves 131 of the fixing shaft 130 while compressing the elastic member 50.

Here, to allow the user to more easily pull the pressure button 710 of the pressure unit 70 in the upward direction, an annular rim 712 may be formed along the edge of the upper end of the pressure button 710 that is exposed outside the top wall of the upper body 12, so that the annular rim 712 protrudes outward from the edge in a radial direction and allows the user to hold the annular rim with fingers.

When the pressure button 710 moves upward as described above, the fixing protrusions 730 are disengaged from the fixing grooves 310 of the bobbin 30 so that the bobbin 30 can rotate reversibly.

In the above state, when the user pulls the dental floss 301 that is exposed outside the dispenser body 10 out of the dispenser body 10, the bobbin 30 rotates reversibly and the dental floss 301 can be pulled out of the dispenser body 10 to a desired length.

When the user removes the upward pulling force from the pressure button 710 of the pressure unit 70, the elastic member 50 elastically expands so that the pressure button 710 having both the fixing protrusions 730 and the vertical movement guide protrusions 711 moves downward in a direction toward the lower body 11 along the vertical movement guide grooves 131 of the fixing shaft 130 by the expansion force of the elastic member 50.

When the pressure button 710 moves downward as described above, the fixing protrusions 730 are brought into engagement with the fixing grooves 310 of the bobbin 30 so that the bobbin 30 cannot rotate reversibly.

Here, because the bobbin 30 cannot rotate reversibly, the dental floss 301 can be prevented from being pulled out of the dispenser body 10.

Figure 8:
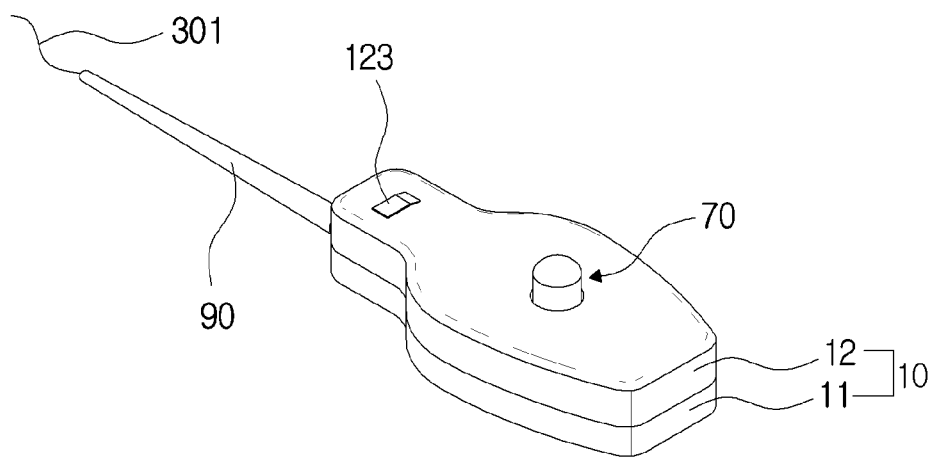
FIG. 8 is a perspective view schematically illustrating an interdental cleaner according to a third embodiment of the present invention.
Figure 9:
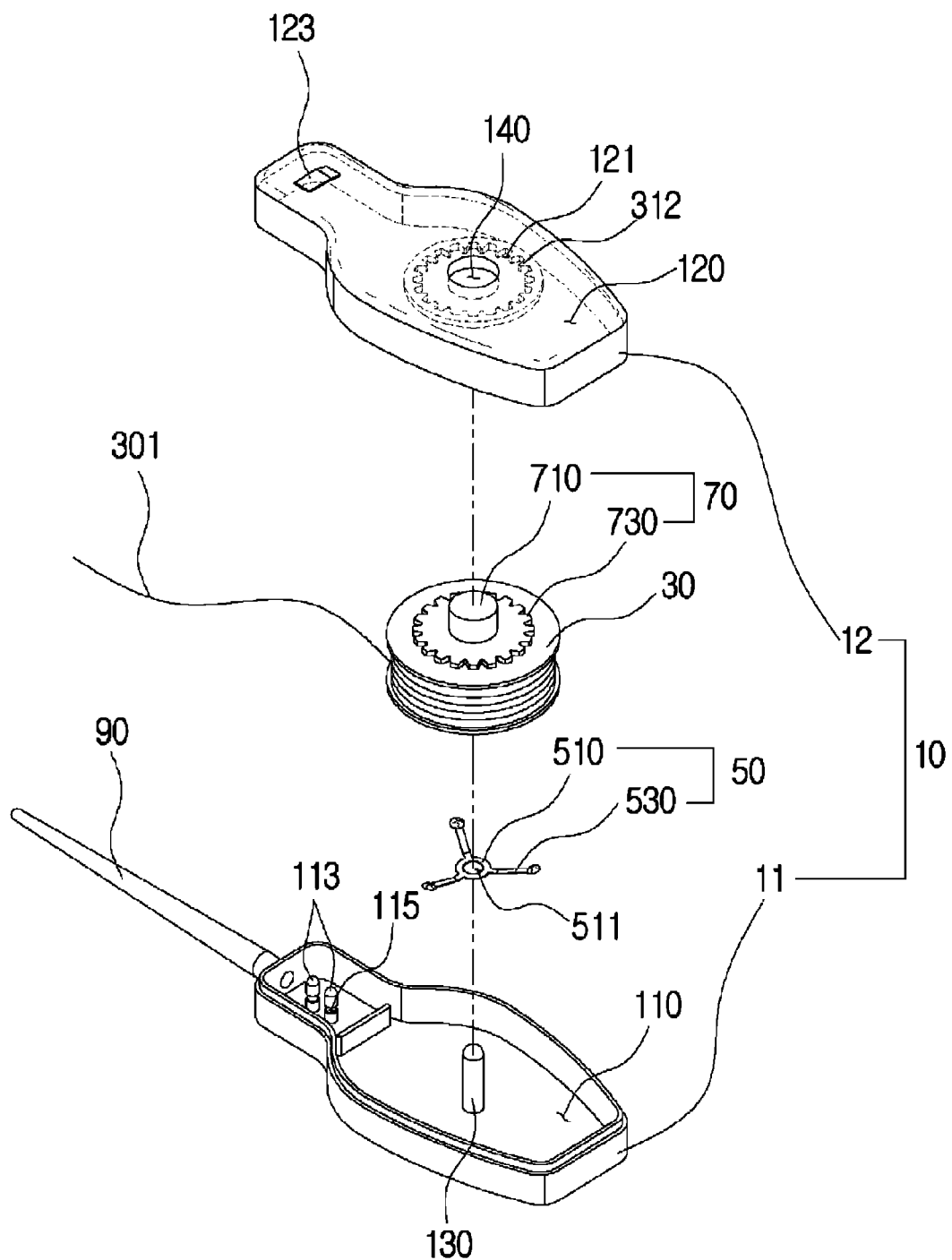
FIG. 9 is an exploded perspective view of FIG. 8.
Figure 10:
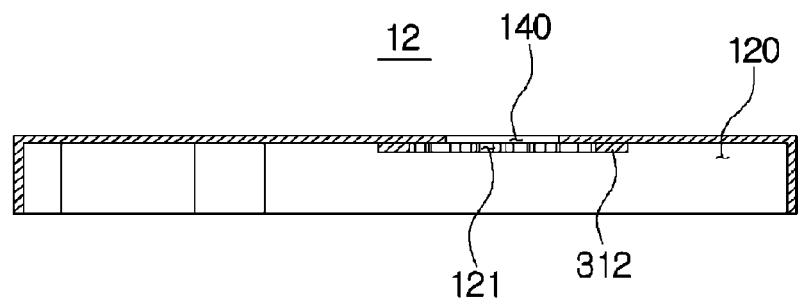
FIG. 10 is a cross-sectional view schematically illustrating a cross-sectioned state of an upper body of a dispenser body.

FIG. 8 is a perspective view schematically illustrating an interdental cleaner according to a third embodiment of the present invention. FIG. 9 is an exploded perspective view of FIG. 8. FIG. 10 is a cross-sectional view schematically illustrating a cross-sectioned state of an upper body of a dispenser body.

As shown in FIGS. 8 and 9, the bobbin 30 may be coupled to the fixing shaft 130 such that the bobbin 30 can rotate reversibly.

Further, as shown in FIG. 10, fixing grooves 121 may be formed at regular intervals on the lower surface of the top wall of the upper body 12 that defines the upper chamber 120 such that the fixing grooves 121 are placed at locations around the through hole 140 of the upper body 12 of the dispenser body 10.

The fixing grooves 121 may be formed between partition ridges 312 which have a triangular shape or another shape and protrude downward from the lower surface of the top wall of the upper body 12 that defines the upper chamber 120, at locations spaced apart from each other at regular intervals.

As shown in FIGS. 8 and 9, the pressure unit 70 may include a pressure button 710 and fixing protrusions 730.

The pressure button 710 is vertically formed on the center of the upper surface of the bobbin 30 so that the pressure button 710 together with the bobbin 30 can move upward and downward in the dispenser body 10.

The upper end of the pressure button 710 may protrude outside the top wall of the upper body 12 of the dispenser body 10 through the through hole 140 of the upper body 12 of the dispenser body 10.

A fixing shaft 130 may be received in the pressure button 710.

The fixing protrusions 730 may be formed at regular intervals around the outer circumferential surface of the upper part of the pressure button 710 in a state in which the fixing protrusions 730 are integrated with the upper surface of the bobbin 30, so that the fixing protrusions 730 are located inside the dispenser body 10 and can be engaged with the fixing grooves 121 of the upper body 12 of the dispenser body 10.

To elastically support the lower surface of the bobbin 30, the elastic member 50 may be placed in the lower body 11 of the dispenser body 10 in a state in which the elastic member 50 surrounds the lower part of the fixing shaft 130 of the lower body 11 of the dispenser body 10.

As shown in FIG. 9, the elastic member 50 may include a seat plate 510 and sloping plates 530.

A through hole 511 may be formed through the center of the seat plate 510.

The through hole 511 may receive the fixing shaft 130 therein.

The sloping plates 530 are formed around the seat plate 510 at regular intervals and elastically support the lower surface of the bobbin 30.

The sloping plates 530 may slope upward in directions from the edge of the seat plate 510 to the outside ends of the sloping plates 530.

Figure 11:
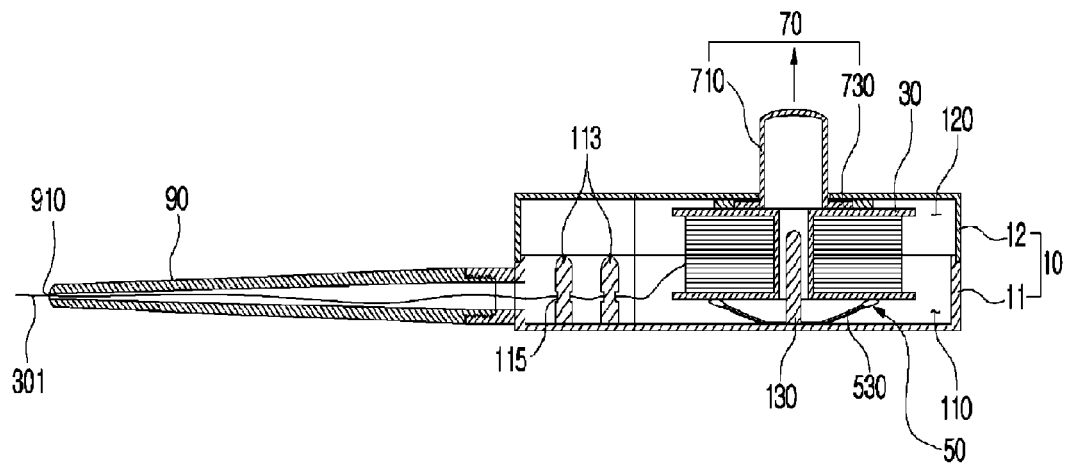
FIGS. 11 and 12 are sectional views schematically illustrating a process of pulling a dental floss out of a dispenser body of FIG. 8.
Figure 12:
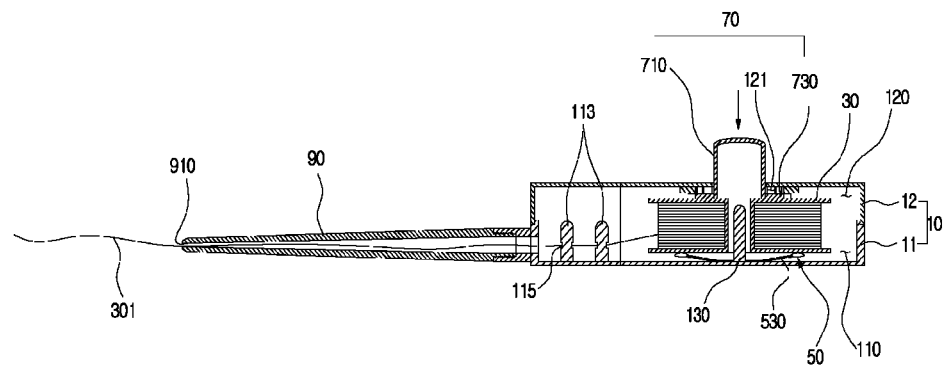

FIGS. 11 and 12 are sectional views schematically illustrating a process of pulling the dental floss 301 out of the dispenser body 10 of FIG. 8.

As shown in FIGS. 11 and 12, when a user presses the pressure button 710 of the pressure unit 70 downward, the pressure button 710 together with the sloping plates 530 of the elastic member 50 and the bobbin 30 moves downward along the fixing shaft 130 in a direction toward the lower body 11.

When the pressure button 710 moves downward as described above, the fixing protrusions 730 are disengaged from the fixing grooves 121 of the upper body 12 of the dispenser body 10 so that the bobbin 30 can rotate reversibly.

In the above state, when the user pulls the dental floss 301 that is exposed outside the dispenser body 10 out of the dispenser body 10, the bobbin 30 rotates reversibly and the dental floss 301 can be pulled out of the dispenser body 10 to a desired length.

When the user removes the force from the pressure button 710 of the pressure unit 70, the sloping plates 530 of the elastic member 50 elastically move upward and the pressure button 710 together with the bobbin 30 moves upward along the fixing shaft 130 in a direction toward the upper body 12 by the elastic upward movement of the sloping plates 530 of the elastic member 50.

When the pressure button 710 moves upward, the fixing protrusions 730 are brought into engagement with the fixing grooves 121 of the upper body 12 of the dispenser body 10 so that the bobbin 30 cannot rotate reversibly.

Because the bobbin 30 cannot rotate reversibly as described above, the dental floss 301 can be prevented from being pulled out of the dispenser body 10.

Figure 13:
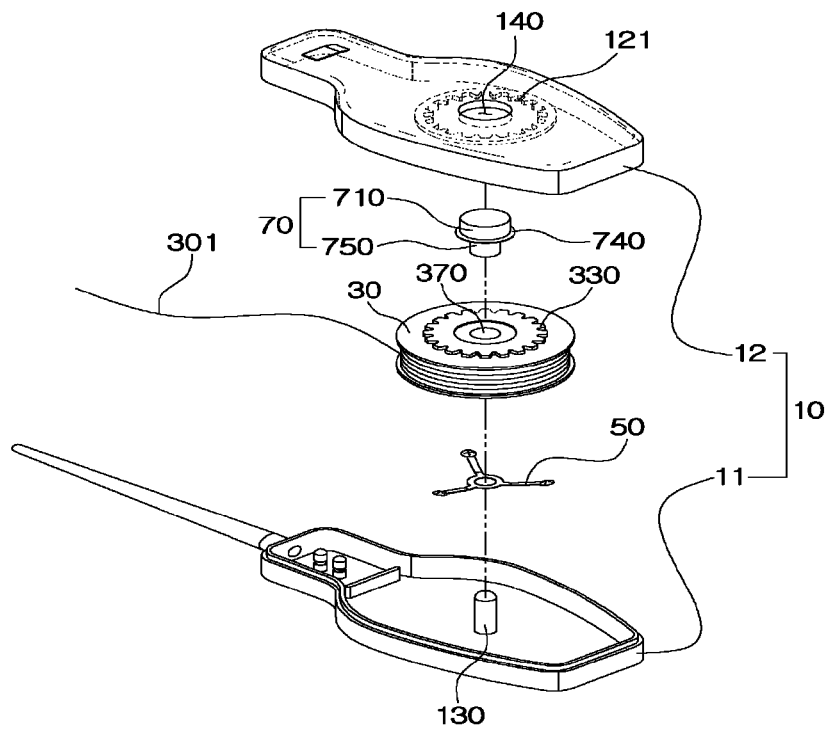
FIG. 13 is an exploded perspective view schematically illustrating an interdental cleaner according to a fourth embodiment of the present invention.
Figure 14:
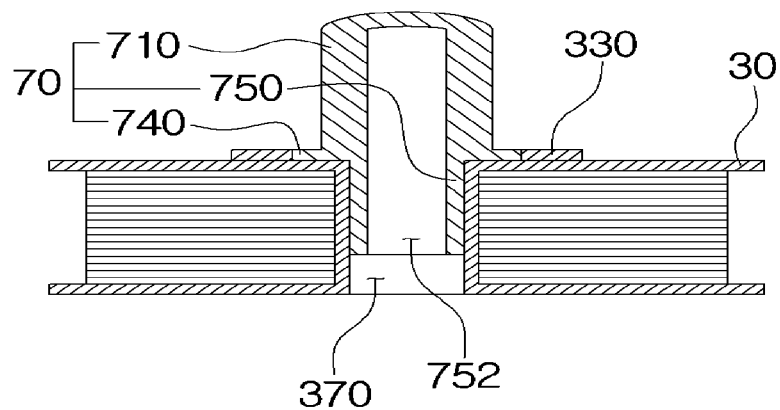
FIG. 14 is a cross-sectional view schematically illustrating a cross-sectioned state of a bobbin in which a pressure unit is placed.

FIG. 13 is an exploded perspective view schematically illustrating an interdental cleaner according to a fourth embodiment of the present invention. FIG. 14 is a cross-sectional view schematically illustrating a cross-sectioned state of a bobbin in which a pressure unit is placed.

Figure 18:
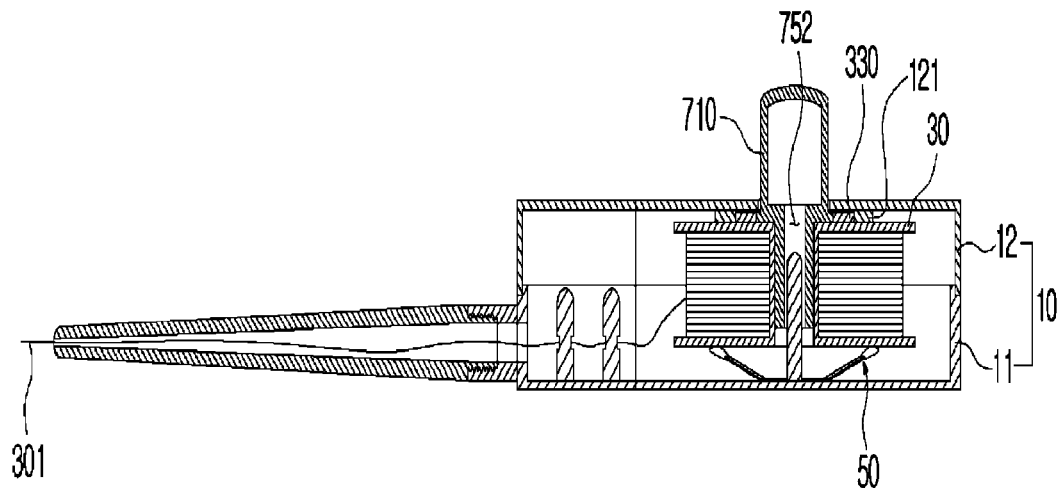
FIGS. 18 and 19 are sectional views schematically illustrating a process of pulling a dental floss out of a dispenser body of FIG. 13.

Unlike the third embodiment, the interdental cleaner according to the fourth embodiment of the present invention is configured such that the pressure button 710 of the pressure unit 70 is not integrated with the bobbin 30, but is separated from the bobbin 30, as shown in FIG. 13. The upper end of the pressure button 710 protrudes outside the through hole 140 of the upper body 12, as shown in FIG. 18.

In order to prevent the pressure button 710 from being undesirably removed from the through hole 140 the upper body 12, it is preferred that an annular protrusion 740 which has an outer diameter greater than the inner diameter of the through hole 140 of the upper body 12 be provided around the lower part of the pressure button 710, as shown in FIG. 13.

Further, as shown in FIGS. 13 and 14, it is preferred that an insert part 750 extend downward from the lower end of the pressure button 710 such that the insert part 750 can be inserted into a shaft hole 370 of the bobbin 30

Further, in order to prevent the bobbin 30 from shaking when the bobbin 30 is rotated in response to a pulling of the dental floss 301 out of the dispenser body 10, it is preferred that the outer diameter of the insert part 750 be slightly smaller than the inner diameter of the shaft hole 370 of the bobbin 30. It is also preferred that the length of the insert part 750 be equal to or slightly shorter that the thickness of the bobbin 30.

Further, as shown in FIG. 18, a hole 752 is axially formed through the insert part 750 such that the fixing shaft 130 of the lower body 11 can be inserted into the hole 752.

Figure 15:
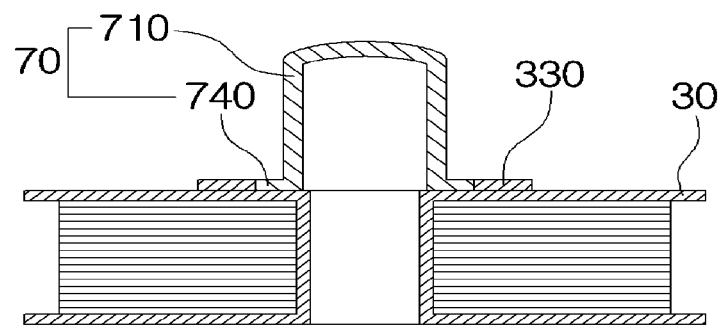
FIG. 15 is a cross-sectional view schematically illustrating a cross-sectioned state of a bobbin in which another type of pressure unit is placed.

FIG. 15 is a cross-sectional view schematically illustrating a cross-sectioned state of a bobbin in which another type of pressure unit is placed.

As shown in FIG. 15, the pressure button of the pressure unit 70 may be configured without having the insert part (750 in FIG. 13).

Figure 16:
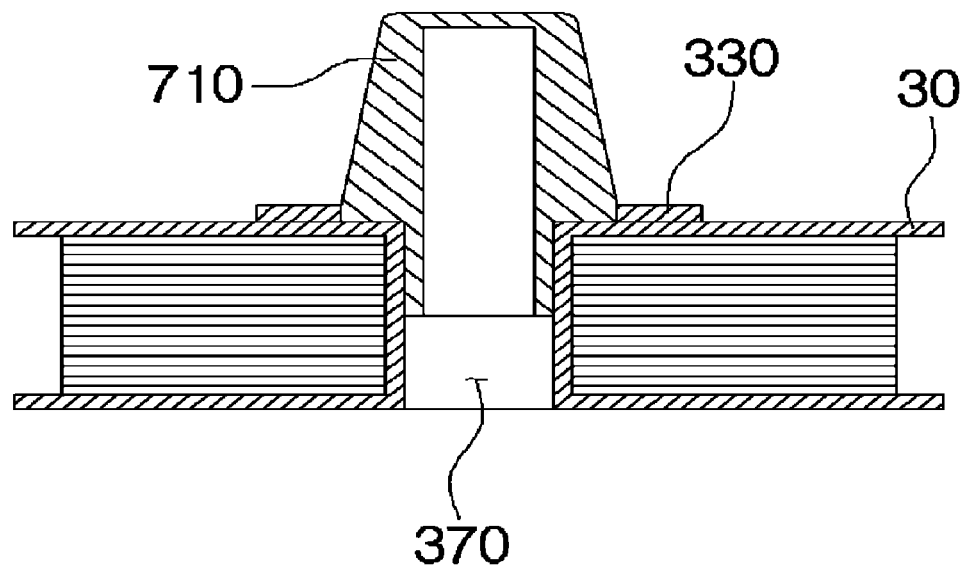
FIG. 16 is a cross-sectional view schematically illustrating a cross-sectioned state of a bobbin in which a further type of pressure unit is placed.
Figure 17:
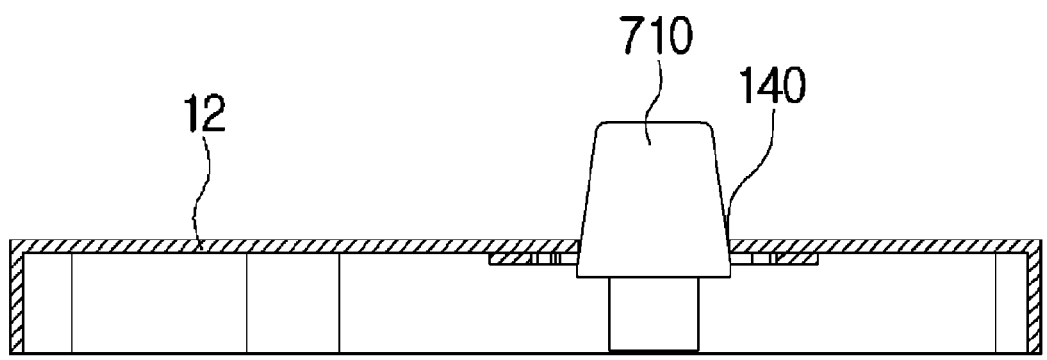
FIG. 17 is a cross-sectional view schematically illustrating a state in which a part of the pressure unit passes through a through hole of the upper body of the dispenser body.

FIG. 16 is a cross-sectional view schematically illustrating a cross-sectioned state of a bobbin in which a further type of pressure unit is placed. FIG. 17 is a cross-sectional view schematically illustrating a state in which a part of the pressure unit passes through a through hole of the upper body of the dispenser body.

As shown in FIG. 16, the pressure unit 710 may be configured as a frusto-conical shape. Further, in order to prevent the pressure button 710 of the pressure unit 710 from being undesirably removed from the through hole 140 of the upper body 12, the pressure button 710 tapers in a direction from the lower end to the upper end, as shown in FIG. 17. Here, the outer diameter of the upper end of the pressure button 710 is smaller than the inner diameter of the through hole 140 of the upper body 12, while the outer diameter of the lower end of the pressure button 710 is greater than the inner diameter of the through hole 140 of the upper body 12.

Further, as shown in FIG. 13, fixing grooves 121 are formed on the upper surface of the upper chamber 120 of the upper body 12 at regular intervals in such a way that the fixing grooves 121 are located around the through hole 140 of the dispenser body 10.

Further, fixing protrusions 330 are formed on the upper surface of the bobbin 30 such that the fixing protrusions 330 can be engaged with the fixing grooves 121 of the dispenser body 10. Further, it is preferred that a receiving groove be formed around the shaft hole 370 of the bobbin 30 such that the annular protrusion 740 of the pressure button 710 can be seated in the receiving groove.

Figure 19:
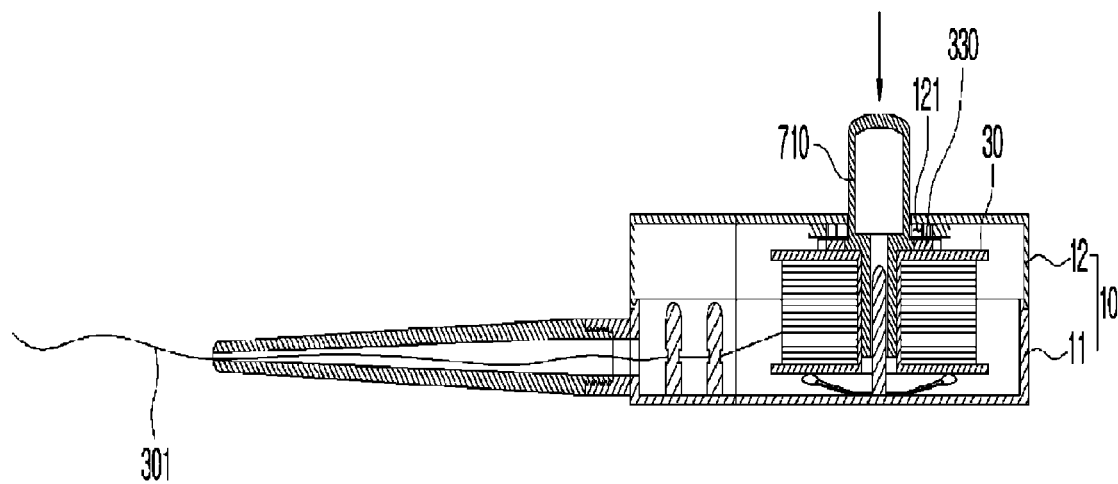

FIGS. 18 and 19 are sectional views schematically illustrating a process of pulling a dental floss out of a dispenser body of FIG. 13;

FIG. 18 is a sectional view illustrating a normal state of the pressure button 710 in which the button 710 is not pressed downward by a finger, etc. In the normal state in which the pressure button 710 is not pressed, as shown in FIG. 18, the fixing protrusions 330 of the bobbin 30 are engaged with the fixing grooves 121 of the upper body 12 due to the elasticity of the elastic member 50 that elastically biases the bobbin 30. Accordingly, the dental floss 301 that is wound around the bobbin 30 is firmly fixed so that, although the dental floss 301 is being strongly pulled, the dental floss 301 cannot be pulled out of the dispenser body.

Further, when the pressure button 710 is pressed downward as shown in FIG. 19, the bobbin 30 is moved downward along with the pressure button 710 so that the fixing protrusions 330 of the bobbin 30 are disengaged from the fixing grooves 121 of the upper body 12, thereby bringing the bobbin 30 into a freely rotatable state. When the dental floss 301 is pulled in the state in which the pressure button 710 is pressed, the bobbin 30 is rotated in a floss unwinding direction and the dental floss 301 is pulled out of the dispenser body 10.

The fourth embodiment, in which the pressure button 710 is not integrated with the bobbin 30, but is separated from the bobbin 30, unlike in the third embodiment, provides the following advantages.

1) when the dental floss 301 is pulled out of the dispenser body 10 in a state in which the pressure button 710 is pressed by a finger, the pressure button 710 that is separated from the bobbin 30 is not rotated, so it is easy to use the interdental cleaner and it is easy to pull the dental floss out of the dispenser body.

2) unlike the third embodiment, in which the shaft hole of the bobbin is closed by the pressure button, making it difficult to install the bobbin in a conventional dental floss winding device, the fourth embodiment, in which the pressure button 710 is separated from the bobbin 30, is advantageous in that it is easy to install the bobbin in the conventional dental floss winding device and it is easy to wind a new dental floss around the bobbin.

Figure 20:
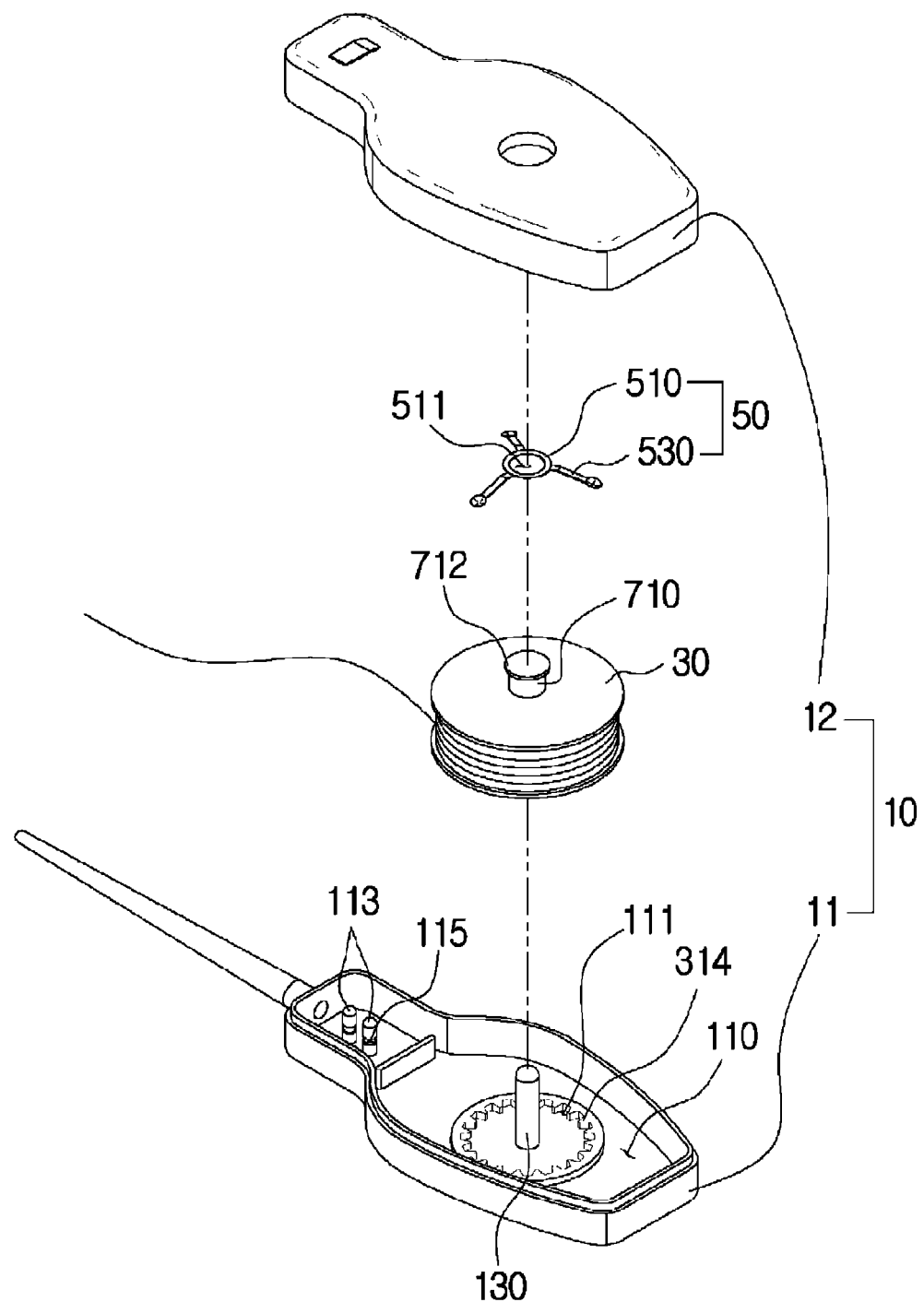
FIG. 20 is an exploded perspective view schematically illustrating an interdental cleaner according to a fifth embodiment of the present invention.
Figure 21:
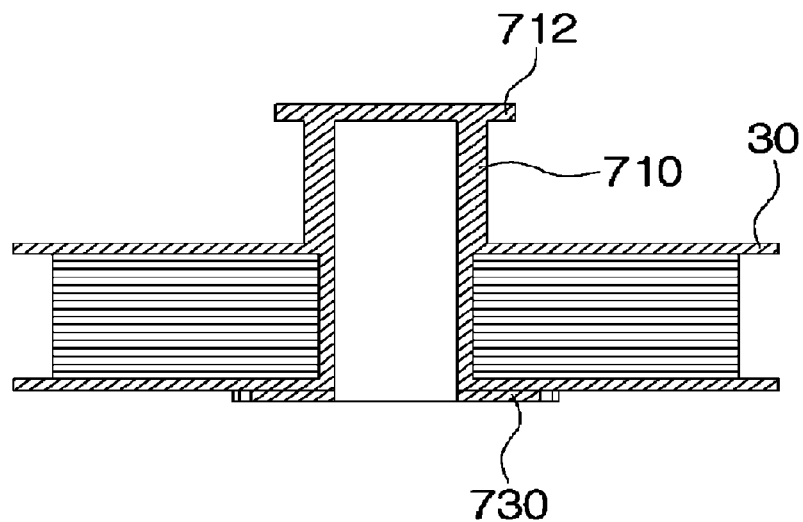
FIG. 21 is a cross-sectional view schematically illustrating a cross-sectioned state of a bobbin in which a pressure unit is placed.
Figure 22:
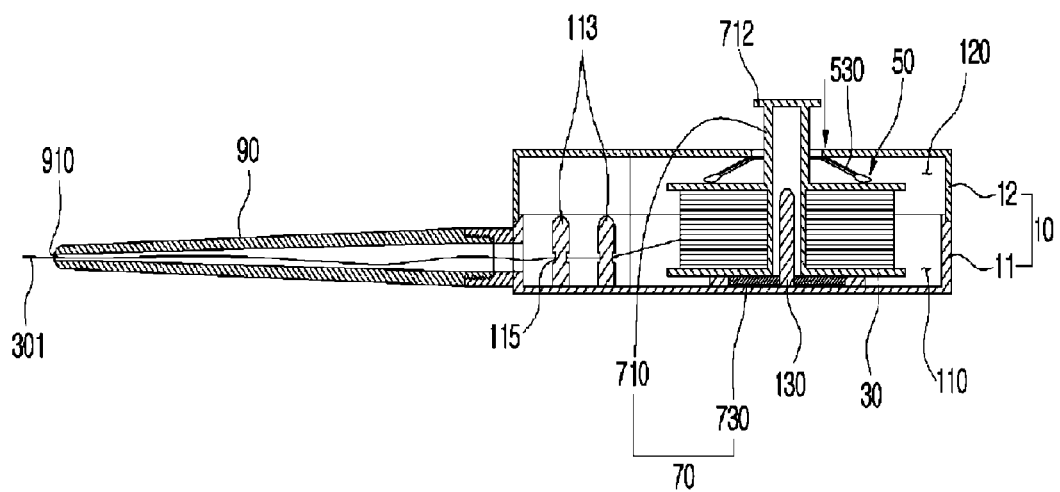
FIGS. 22 and 23 are sectional views schematically illustrating a process of pulling a dental floss out of a dispenser body of FIG. 20.
Figure 23:
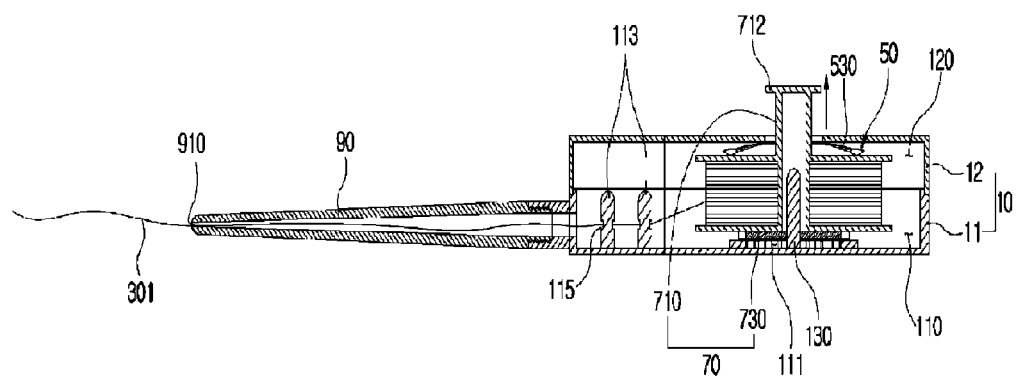

FIG. 20 is an exploded perspective view schematically illustrating an interdental cleaner according to a fifth embodiment of the present invention. FIG. 21 is a cross-sectional view schematically illustrating a cross-sectioned state of a bobbin in which a pressure unit is placed. FIGS. 22 and 23 are sectional views schematically illustrating a process of pulling a dental floss 301 out of a dispenser body 10 of FIG. 20.

As shown in FIG. 20, fixing grooves 111 may be formed on the bottom surface of the lower chamber 110 of the lower body 11 at regular intervals so that the fixing grooves 111 are placed at locations around the fixing shaft 130 of the lower body 11 of the dispenser body 10.

The fixing grooves 111 may be formed between partition ridges 314 which have a triangular shape or another shape and protrude upward from the bottom surface of the lower chamber 110 at locations spaced apart from each other at regular intervals.

As described above, the pressure unit 70 may include a pressure button 710 and fixing protrusions 730.

Here, as shown in FIG. 21, the fixing protrusions 730 may be formed at locations around the center of the lower surface of the bobbin 30 at regular intervals in a state in which the fixing protrusions 730 are integrated with the lower surface of the bobbin 30 so that the fixing protrusions 730 can be engaged with the fixing grooves 111 of the lower body 11 of the dispenser body 10.

To elastically support the upper surface of the bobbin 30, the elastic member 50 may be placed in the upper body 12 of the dispenser body 10 in a state in which the elastic member 50 surrounds the pressure button 710.

Here, the upper part of the pressure button 710 may pass through the through hole 511 of the seat plate 510 of the elastic member 50.

The sloping plates 530 of the elastic member 50 may slope downward in directions from the edge of the seat plate 510 to the outside ends of the sloping plates 530 so that the sloping plates 530 can elastically support the upper surface of the bobbin 30.

As shown in FIGS. 22 and 23, when a user holds the annular rim 712 with fingers and pulls the pressure button 710 of the pressure unit 70 upward, the pressure button 710 together with the sloping plates 530 of the elastic member 50 and the bobbin 30 moves upward along the fixing shaft 130 in a direction toward the upper body 12.

When the pressure button 710 moves upward as described above, the fixing protrusions 730 are disengaged from the fixing grooves 111 of the lower body 11 of the dispenser body 10 so that the bobbin 30 can rotate reversibly.

In the above state, when the user pulls the dental floss 301 that is exposed outside the dispenser body 10 out of the dispenser body 10, the bobbin 30 rotates reversibly and the dental floss 301 can be pulled out of the dispenser body 10 to a desired length.

When the user removes the upward pulling force from the pressure button 710 of the pressure unit 70, the sloping plates 530 of the elastic member 50 move downward and the pressure button 710 together with the bobbin 30 moves downward along the fixing shaft 130 in a direction toward the lower body 11 by the downward moving force of the sloping plates 530 of the elastic member 50.

When the pressure button 710 moves downward as described above, the fixing protrusions 730 are engaged with the fixing grooves 111 of the lower body 11 of the dispenser body 10 so that the bobbin 30 cannot rotate reversibly.

Here, because the bobbin 30 cannot rotate reversibly, the dental floss 301 is prevented from being pulled out of the dispenser body 10.

As described above, the present invention is advantageous in that it can more efficiently control the reversible rotation of the bobbin 30 using the pressure unit 70 having both the pressure button 710 and the fixing protrusions 730.

Further, as shown in FIGS. 3, 4, 6, 7, 11, 12, 22 and 23, one shaft 113 or at least two shafts 113 may be vertically formed on a part of the bottom surface of the lower chamber 110 of the lower body 11 of the dispenser body 10 so that a user can wind the dental floss 301 of the bobbin 30 at least once. Here, when at least two shafts 113 are provided, the shafts are spaced apart from each other by a predetermined distance.

Figure 24:
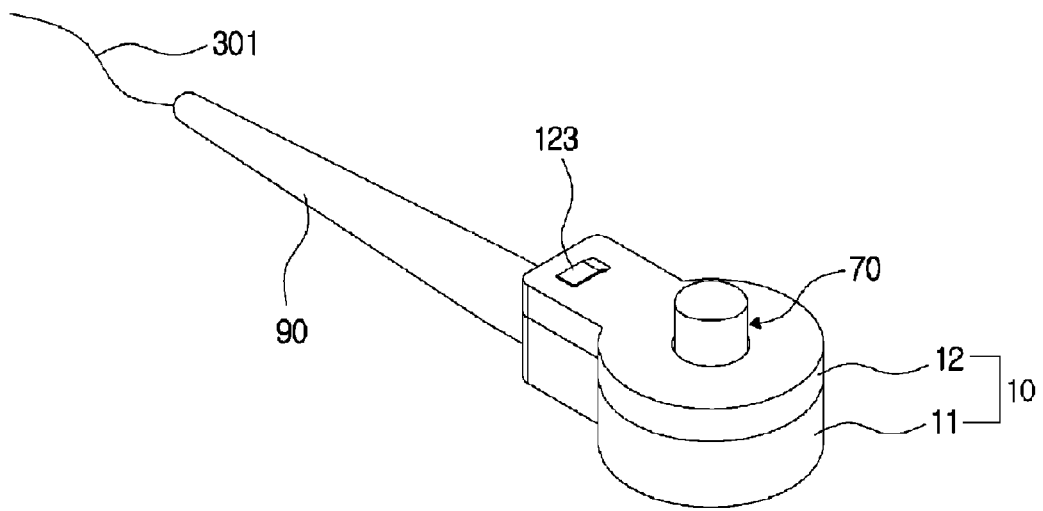
FIG. 24 is a perspective view schematically illustrating an interdental cleaner in which a tip is integrated with a dispenser body into a single body.

FIG. 24 is a perspective view schematically illustrating an interdental cleaner in which a tip 90 is integrated with a dispenser body 10 into a single body.

As shown in FIG. 24, the tip 90 may be integrally formed with the dispenser body 10 so that the tip 90 can communicate with the dispenser body 10.

One end of the tip 90 has an outlet hole 910 through which the dental floss 301 that is wound around the shaft 113 at least once can be pulled out.

Here, a user can pull the dental floss 301 that is wound around the shaft 113 at least once out of the dispenser body 10 having the tip 90 to a desired length through the outlet hole 910.

The dental floss 301 is wound at least once around the shaft 113 that is vertically formed on a part of the bottom surface of the lower chamber 110 of the dispenser body 10, so that the bobbin 30, which rotates reversibly during a floss pulling process in which the dental floss 301 is pulled out of the dispenser body 10 through the outlet hole 910 of the tip 90 by a user, can be more efficiently prevented from moving upward and downward Further, as shown in FIGS. 3 and 4, a second end of the tip 90 may be combined with the internally threaded hole, which is formed in a first end of the lower body 11 of the dispenser body 10, through a screw type engagement by a user so that the tip 90 can be more simply and more firmly combined with the first end of the lower body 11 of the dispenser body 10.

Further, as shown in FIG. 2, on the inner circumferential surface of the first end of the lower body 11 of the dispenser body 10, a guide groove 112 and a locking groove 114 may be formed in such a way that the grooves 112 and 114 are depressed to predetermined depths in a direction toward the outer circumferential surface of the first end of the lower body 11 of the dispenser body 10.

The guide groove 112 may be formed by axially extending on the inner circumferential surface of the first end of the lower body 11 of the dispenser body 10.

The guide groove 112 may comprise front and rear guide grooves 112a and 112b that axially extend on the front and rear parts of the inner circumferential surface of the first end of the lower body 11 of the dispenser body 10, respectively.

The locking groove 114 may comprise front and rear locking grooves 114a and 114b that vertically extend from the second ends of the front and rear guide grooves 112a and 112b, respectively, so that the front and rear locking grooves 114a and 114b communicate with the front and rear guide grooves 112a and 112b, respectively.

The front locking groove 114a may vertically extend downward from the second end of the front guide groove 112a in such a way that the upper end of the front locking groove 114a communicates with the second end of the front guide groove 112a The rear locking groove 114b may vertically extend upward from the second end of the rear guide groove 112b in such a way that the lower end of the rear locking groove 114b communicates with the second end of the rear guide groove 112b As shown in FIG. 2, a locking protrusion 930 protrudes on the outer circumferential surface of the second end of the tip 90 in a radially outward direction from the second end of the tip 90 so that the locking protrusion 930 can axially move along the guide groove 112 and can be locked in the locking groove 114 by a user.

The locking protrusion 930 may comprise front and rear locking protrusions 931 and 933.

The front locking protrusion 931 may protrude on the front part of the second end of the tip 90 in the radially outward direction so that, when the user reversibly rotates the tip 90, the front locking protrusion 931 can be locked in the front locking groove 114a.

The rear locking protrusion 933 may protrude on the rear part of the second end of the tip 90 in the radially outward direction so that, when the user reversibly rotates the tip 90, the rear locking protrusion 933 can be locked in the rear locking groove 114b.

When both the guide groove 112 and the locking groove 114 are formed on the inner circumferential surface of the first end of the lower body 11 of the dispenser body 10, and the locking protrusion 930 is formed on the outer circumferential surface of the second end of the tip 90 in such a way that, when the user axially moves the locking protrusion 930 along the guide groove 112 and rotates the locking protrusion 930, the locking protrusion 930 can be locked in the locking groove 114, the tip 90 can be more easily and more firmly assembled with the first end of the dispenser body 10 through a one touch assembly process.

Figure 25:
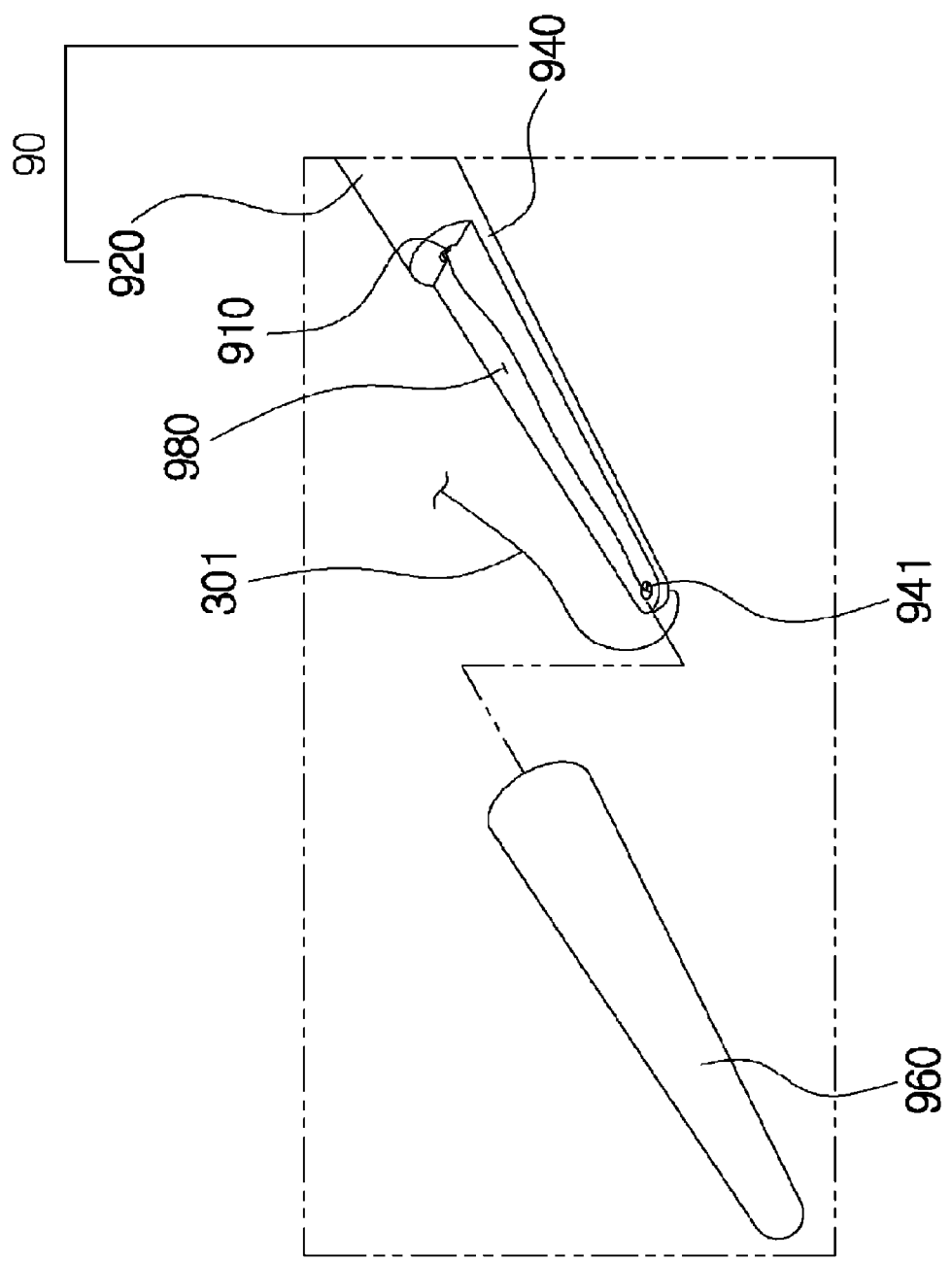
FIGS. 25 and 26 are perspective views schematically illustrating an interdental cleaner in which a tip is fabricated with a first tip part and a second tip part.
Figure 26:
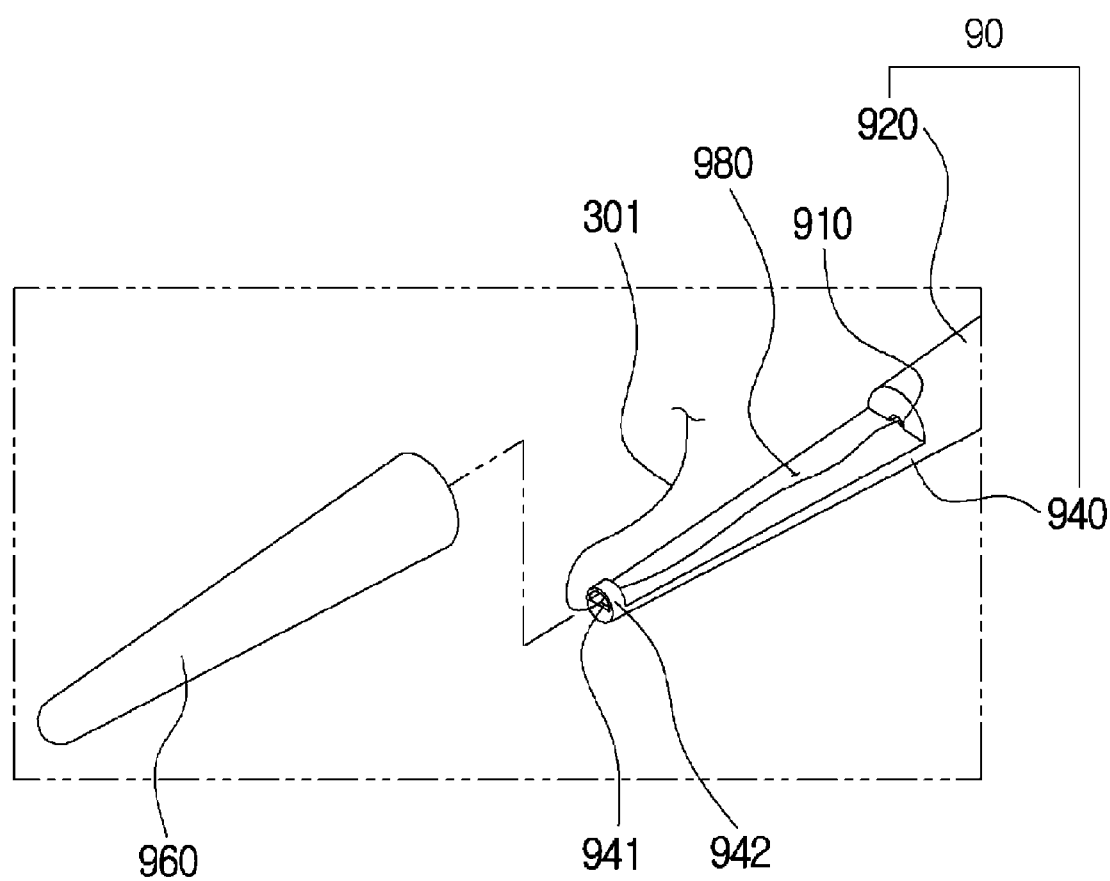

FIGS. 25 and 26 are perspective views schematically illustrating the tip 90 that comprises a second tip part 920 and a first tip part 940.

As shown in FIGS. 25 and 26, the tip 90 may comprise the second tip part 920 and the first tip part 940.

The second tip part 920 may horizontally extend from the first end of the lower body 11 of the dispenser body 10 in such a way that the second tip part 920 can communicate with the lower body 11 of the dispenser body 10.

The second tip part 920 may have a circular cross-section or an elliptical cross-section.

The first tip part 940 may integrally and horizontally extend from a lower part of the first end of the second tip part 920 in such a way that the first tip part 940 can communicate with the second tip part 920.

The inner diameter of the first tip part 940 may be smaller than the inner diameter of the second tip part 920.

In the first tip part 940, the upper surface may be a horizontal flat surface, and the lower surface may be a downward round surface so that the lower surface forms a semicircular cross-section.

In an upper part of an end surface of the second tip part 920, the outlet hole 910, through which the dental floss 301 wound around the shaft 113 can be pulled out, may be formed.

The dental floss 301 that has passed through the outlet hole 910 may be located on an L-shaped step part 980 that is defined between the upper surface of the first tip part 940 and a side surface of the second tip part 920.

A through hole 941 may be formed in the first end of the first tip part 940 so that the dental floss 301 passes through the through hole 941 after the floss 301 is pulled out through the outlet hole 910.

As shown in FIG. 25, the through hole 941 may be formed in such a way that the through hole 941 is open upward and downward in the first end of the first tip part 940.

Alternatively, as shown in FIG. 26, the through hole 941 may be formed in such a way that the through hole 941 is defined in a ring part 942 that is integrally formed on the upper surface of the first end of the first tip part 90.

The ring part 942 may be convex upward so that the ring part 942 has a semicircular cross-section.

To prevent the step part 980 from being exposed to the outside, a cover 960 may be detachably mounted to the first tip part 940 in a state in which the cover 940 covers parts of the first ends of the first tip part 940 and the second tip part 920 of the tip 90.

As shown in FIGS. 3, 4, 6, 7, 11, 12, 22 and 23, an annular groove 115 is formed around the central portion of the outer circumferential surface of the shaft 113. This annular groove 115 is formed by depressing the outer circumferential surface of the shaft 113 to a predetermined depth in a radial direction.

The dental floss 301 can be held in the annular groove 115 in a state in which the dental floss 301 is wound around the annular groove 115 at least once.

Because the dental floss 301 is held in the annular groove 115 on the outer circumferential surface of the shaft 113 in a state in which the dental floss 301 is wound around the annular groove 115 at least once, the dental floss 301 can be more efficiently prevented from being removed from the shaft 113.

Figure 27:
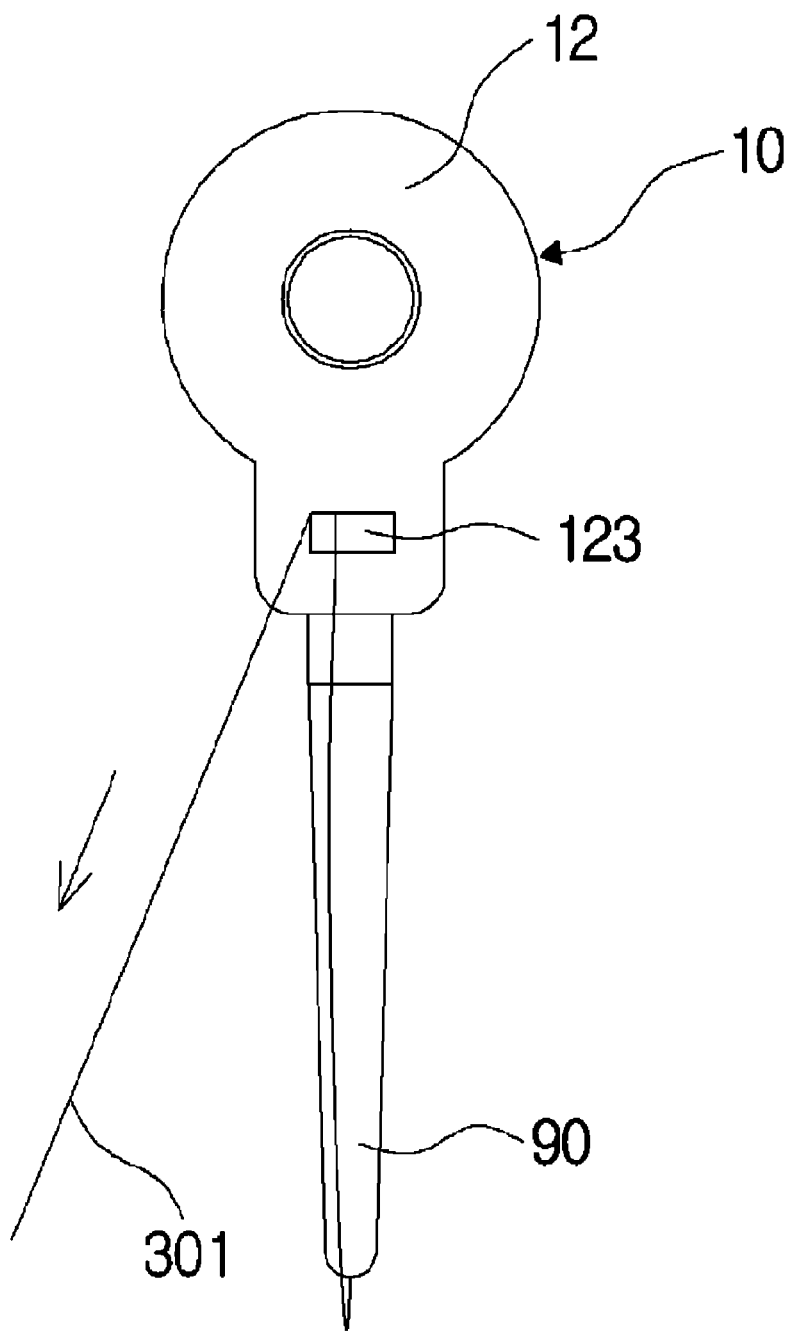
FIG. 27 is a view schematically illustrating a process of cutting the dental floss using a cutting member.

FIG. 27 is a view schematically illustrating a process of cutting the dental floss 301 using a cutting member 123.

As shown in FIG. 27, a cutting member 123 may be provided in the first end of the top wall of the upper body 12 of the dispenser body 10 so that the cutting member 123 can cut the dental floss 301 that has been pulled out of the dispenser body 10 to a desired length through the outlet hole 910 of the tip 90.

The cutting member 123 may be formed in the first end of the top wall of the upper body 12 of the dispenser body 10 so that the cutting member 123 may have an L-shape or another shape.

The user can cut the dental floss 301 that has been pulled out of the dispenser body 10 to a desired length by momentarily pulling the floss 301 downward (see the solid arrow in FIG. 27) in a state in which the floss 301 is received in the cutting member 123.

The present invention is advantageous in that it can more easily cut the dental floss 301, which has been pulled out of the dispenser body 10 to a desired length, using the cutting member 123 that is formed in the first end of the top wall of the upper body 12 of the dispenser body 10.

The present invention having the above-mentioned construction is advantageous in that the pressure unit 70 moves upward and downward in the dispenser body 10 and controls the rotation of the bobbin 30 so that the present invention can firmly hold the dental floss 301 that has been pulled out of the dispenser body 10 to a desired length, thereby preventing the dental floss 301 from being further pulled out and preventing the dental floss 301 from being undesirably pulled out when a user uses the floss 301, that is, the present invention preventing a slip of the dental floss 301.

The invention claimed is:

1. An interdental cleaner, comprising:
a dispenser body including a lower body having therein an upward open lower chamber, with a fixing shaft being vertically formed on a bottom surface of the lower chamber, and an upper body placed on the lower body and having therein a downward open upper chamber, with a through hole being formed through a top wall of the upper body so as to communicate with the lower chamber;
a bobbin provided in the dispenser body in such a way that the bobbin is fitted over the fixing shaft of the dispenser body, with a dental floss being wound around the bobbin;
an elastic member provided in the dispenser body; and
a pressure unit provided in the dispenser body in such a way that the pressure unit is configured to move upward and downward in the dispenser body by elasticity of the elastic member so that the pressure unit is configured to control a rotation of the bobbin and an upper end of the pressure unit protrudes outside the dispenser body through the through hole of the dispenser body,
wherein fixing grooves are formed at regular intervals on a lower surface of the top wall of the upper body that defines the upper chamber such that the fixing grooves are placed at locations around the through hole of the dispenser body, and
wherein the pressure unit comprises a pressure button, in which an upper end of the pressure button protrudes outside the dispenser body through the through hole of the dispenser body,
wherein fixing protrusions are formed on an upper surface of the bobbin such that the fixing protrusions are engaged with the fixing grooves of the upper body, and
wherein the elastic member is placed in the dispenser body in a state in which the elastic member surrounds a lower part of the fixing shaft of the dispenser body so as to elastically support a lower surface of the bobbin.

2. The interdental cleaner as set forth in claim 1, wherein a shaft is vertically formed on a part of the bottom surface of the lower chamber of the dispenser body so that the dental floss of the bobbin can be wound around the shaft, and
a tip is provided in the dispenser body, with an outlet hole being formed in a first end of the tip so as to allow the dental floss wound around the shaft to be pulled out through the outlet hole.

3. The interdental cleaner as set forth in claim 2, wherein a second end of the tip is combined with a first end of the dispenser body through a screw type engagement.

4. The interdental cleaner as set forth in claim 2, wherein a guide groove is formed on an inner circumferential surface of a first end of the dispenser body by axially extending,
a locking groove is formed on the inner circumferential surface of the first end of the dispenser body by vertically extending from a second end of the guide groove so as to communicate with the guide groove, and
a locking protrusion protrudes on an outer circumferential surface of a second end of the tip in a radially outward direction from the second end of the tip so that the locking protrusion can axially move along the guide groove and can be locked in the locking groove.

5. The interdental cleaner as set forth in claim 2, wherein the tip comprises a second tip part that is provided on a first end of the dispenser body; and a first tip part that is provided on a first end of the second tip part, with an inner diameter of the first tip part being smaller than an inner diameter of the second tip part, wherein
the outlet hole is formed on an end surface of the second tip part so as to allow the dental floss wound around the shaft to be pulled out through the outlet hole, and
a through hole is formed in a first end of the first tip part so that the dental floss passes through the through hole after the floss is pulled out through the outlet hole.

6. The interdental cleaner as set forth in claim 2, wherein an annular groove is formed around an outer circumferential surface of the shaft so as to hold the dental floss.

7. An interdental cleaner,
comprising:
a dispenser body including a lower body having therein an upward open lower chamber, with a fixing shaft being vertically formed on a bottom surface of the lower chamber, and an upper body placed on the lower body and having therein a downward open upper chamber, with a through hole being formed through a top wall of the upper body so as to communicate with the lower chamber;
a bobbin provided in the dispenser body in such a way that the bobbin is fitted over the fixing shaft of the dispenser body, with a dental floss being wound around the bobbin;
an elastic member provided in the dispenser body; and
a pressure unit provided in the dispenser body in such a way that the pressure unit is configured to move upward and downward in the dispenser body by elasticity of the elastic member so that the pressure unit is configured to control a rotation of the bobbin and an upper end of the pressure unit protrudes outside the dispenser body through the through hole of the dispenser body,
wherein vertical movement guide grooves are vertically formed at regular intervals around an outer circumferential surface of the fixing shaft of the dispenser body; and
fixing grooves are formed at regular intervals around an upper part of an inner circumferential surface of the bobbin,
wherein the pressure unit comprises:
a pressure button that is vertically movably received in the bobbin so that an upper end of the pressure button protrudes outside the dispenser body through the through hole of the dispenser body, with vertical movement guide protrusions being formed at regular intervals around a lower part of an inner circumferential surface of the pressure button so as to be engaged with the vertical movement guide grooves of the fixing shaft; and
fixing protrusions that are formed at regular intervals around a lower part of an outer circumferential surface of the pressure button so as to be engaged with the fixing grooves of the bobbin, and
wherein the elastic member is provided in a lower part inside the dispenser body such that the elastic member is placed in the bobbin in a state in which the elastic member surrounds a lower end of the fixing shaft of the dispenser body so as to elastically support a lower end of the pressure button.

8. An interdental cleaner,
comprising:
a dispenser body including a lower body having therein an upward open lower chamber, with a fixing shaft being vertically formed on a bottom surface of the lower chamber, and an upper body placed on the lower body and having therein a downward open upper chamber, with a through hole being formed through a top wall of the upper body so as to communicate with the lower chamber;

a bobbin provided in the dispenser body in such a way that the bobbin is fitted over the fixing shaft of the dispenser body, with a dental floss being wound around the bobbin;

an elastic member provided in the dispenser body; and a pressure unit provided in the dispenser body in such a way that the pressure unit is configured to move upward and downward in the dispenser body by elasticity of the elastic member so that the pressure unit is configured to control a rotation of the bobbin and an upper end of the pressure unit protrudes outside the dispenser body through the through hole of the dispenser body, wherein fixing grooves are formed at regular intervals on a lower surface of the top wall of the upper body that defines the upper chamber such that the fixing grooves are placed at locations around the through hole of the dispenser body, wherein the pressure unit includes:

a pressure button that is vertically formed on a center of an upper surface of the bobbin and moves upward and downward in the dispenser body together with the bobbin so that an upper end of the pressure button protrudes outside the dispenser body through the through hole of the dispenser body; and fixing protrusions that are formed at regular intervals around an outer circumferential surface of an upper part of the pressure button in a state in which the fixing protrusions are integrated with the upper surface of the bobbin so that the fixing protrusions are engaged with the fixing grooves of the dispenser body, and wherein the elastic member is placed in the dispenser body in a state in which the elastic member surrounds a lower part of the fixing shaft of the dispenser body so as to elastically support a lower surface of the bobbin.

* * * * *